United States Patent
McChesney et al.

(10) Patent No.: US 9,896,403 B2
(45) Date of Patent: Feb. 20, 2018

(54) SOLUBILIZATION OF PTEROSTILBENE AND RESVERATROL IN AQUEOUS BEVERAGES

(71) Applicant: Ironstone Separations, Inc., Etta, MS (US)

(72) Inventors: James D. McChesney, Etta, MS (US); Igor Nikoulin, La Jolla, CA (US); Douglas L. Rodenburg, Thaxton, MS (US)

(73) Assignee: Ironstone Separations, Inc., Etta, MS (US)

( * ) Notice: Subject to any disclaimer, the term of this patent is extended or adjusted under 35 U.S.C. 154(b) by 195 days.

(21) Appl. No.: 14/466,922

(22) Filed: Aug. 22, 2014

(65) Prior Publication Data

US 2016/0052850 A1    Feb. 25, 2016

(51) Int. Cl.
*A23L 2/52* (2006.01)
*C07C 43/23* (2006.01)
*A23L 33/105* (2016.01)

(52) U.S. Cl.
CPC ............... *C07C 43/23* (2013.01); *A23L 2/52* (2013.01); *A23L 33/105* (2016.08); *C07B 2200/13* (2013.01)

(58) Field of Classification Search
CPC ..... A23L 2/52; A23L 33/105; C07B 2200/13; C07C 43/23
See application file for complete search history.

(56) References Cited

U.S. PATENT DOCUMENTS

| | | | | |
|---|---|---|---|---|
| 6,458,373 | B1* | 10/2002 | Lambert | A61K 9/0019 424/405 |
| 2011/0189278 | A1* | 8/2011 | Schultheiss | C07D 473/12 424/465 |

* cited by examiner

*Primary Examiner* — Snigdha Maewall
(74) *Attorney, Agent, or Firm* — Hamilton Desanctis & Cha, LLP; Sam L. Nguyen

(57) ABSTRACT

In one embodiment, the present application discloses compositions and methods of solubilizing pterostilbene or resveratrol, or mixture thereof in aqueous media.

3 Claims, No Drawings

SOLUBILIZATION OF PTEROSTILBENE AND RESVERATROL IN AQUEOUS BEVERAGES

RELATED APPLICATION

This application claims the benefit of U.S. Provisional Application No. 61/872,971, filed Sep. 3, 2013, which is incorporated herein by reference.

SUMMARY

Pterostilbene (trans-3,5-dimethoxy-4-hydroxystilbene) and resveratrol are natural dietary compounds and the primary antioxidant component of blueberries, among other fruits. Pterostilbene has increased oral bioavailability in comparison to other stilbene compounds, which may enhance its dietary benefit and possibly contribute to advantageous clinical effect. Multiple studies have demonstrated the antioxidant activity of resveratrol and pterostilbene in both in vitro and in vivo models illustrating both preventative and therapeutic benefits. The antioxidant activity of resveratrol and pterostilbene has been implicated in anticarcinogenesis, modulation of neurological disease, anti-inflammation, attenuation of vascular disease, and amelioration of diabetes. Solubility of pterostilbene in aqueous media is very low which is limiting of its incorporation into beverages for convenient consumption. We have discovered a methodology to solubilize resveratrol and pterostilbene for inclusion in beverages which provides a safe and an efficient delivery of a wide range of resveratrol and pterostilbene doses.

BACKGROUND

Pterostilbene (trans-3,5-dimethoxy-4-hydroxystilbene) is a naturally derived compound found in blueberries. The amount of daily pterostilbene consumption varies according to dietary fruit intake, and it has been estimated that pterostilbene content in blueberry varies from 99 ng to 520 ng/gram depending on the variety of berry ingested. Substantial evidence suggests that pterostilbene may have numerous preventive and therapeutic properties in a vast range of human diseases that include neurological, cardiovascular, metabolic and hematologic disorders (D. McCormack and D. McFadden, 2013, A Review of Pterostilbene Antioxidant and Disease Modification, Oxidative Medicine and Cell Longevity, http://dx.doi.org/10.1155/2013/575482. Further benefits of pterostilbene have been reported in preclinical trials, in which pterostilbene was shown to be a potent anticancer agent in several malignancies (D. McCormack and D. McFadden, "Pterostilbene and cancer: current review," Journal of Surgical Research, vol. 173, no. 2, pp. 53-61, 2012). Pterostilbene is structurally similar to resveratrol, a compound found in red wine that has comparable antioxidant, anti-inflammatory, and anticarcinogenic properties; however, pterostilbene exhibits increased absorption due to the presence of two methoxy groups which cause it to exhibit increased lipophilicity and oral bioavailability. In animal studies, pterostilbene was shown to have 80% bioavailability compared to 20% for resveratrol making it potentially advantageous as a therapeutic agent. The multiple benefits of pterostilbene in the treatment and prevention of human disease have been attributed to its antioxidant, anti-inflammatory, and anticarcinogenic properties leading to improved function of normal cells and inhibition of malignant cell. The evidence reviewed by McCormack and McFadden shows that pterostilbene reduces oxidative stress (OS) and production of reactive oxygen species (ROS), such as hydrogen peroxide ($H_2O_2$) and superoxide anion ($O_2-$), which are implicated in the initiation and pathogenesis of several disease processes. In addition, various cell lines treated with pterostilbene have shown increased expression of the antioxidants catalase, total glutathione (GSH), glutathione peroxidase (GPx), glutathione reductase (GR) and superoxide dismutase (SOD).

Resveratrol (3,5,4'-trihydroxy-trans-stilbene) is a stilbenoid, a type of natural phenol and a phytoalexin produced naturally by several plants.

That the many observed benefits of pterostilbene ingestion be realized for people, it is necessary that convenient dosage forms be developed. Various beverages are popular with consumers for consumption; sports drinks, vitamin waters, fruit juices, energy drinks, etc. However, the near insolubility of pterostilbene in aqueous solutions precludes the ready incorporation of resveratrol or pterostilbene into these popular beverages.

SUMMARY OF THE INVENTION

In one embodiment, the application discloses a stable and homogeneous aqueous composition comprising: a) a compound selected from the group consisting of resveratrol and pterostilbene; and b) an emulsifying agent in an amount sufficient to solubilize resveratrol or pterostilbene to form the stable and homogeneous composition. In another embodiment, there is provided a A stable and homogeneous aqueous formulation comprising: a) a composition selected from the group consisting of a pterostilbene-caffeine co-crystal complex, a resveratrol-caffeine co-crystal complex and a mixture thereof; and b) an emulsifying agent in an amount sufficient to solubilize the pterostilbene-caffeine co-crystal complex, a resveratrol-caffeine co-crystal complex and a mixture thereof, to form the stable and homogeneous formulation. In one aspect, the stable and homogeneous aqueous composition further comprises caffeine. In one aspect, the composition is water soluble. In another aspect of the composition, the resveratrol and caffeine is a co-crystal complex or the pterostilbene and caffeine is a co-crystal complex. In another aspect, the composition further comprises an emulsifying agent selected from the group consisting of TPGS, TPGS-300, TPGS-500, TPGS-600, TPGS-750, TPGS-1000, TPGS-M, TPGS-300-M, TPGS-500-M, TPGS-600-M, TPGS-750-M and TPGS-1000-M, or a mixture thereof. In another aspect of the above the composition is an emulsion, a concentrated emulsion or a clear solution in water.

As disclosed herein, the composition is stable, that is, does not result in decomposition and/or precipitation for a period of at least 6 months or 12 months at RT, or at least 12 months at about 12-15° C. The stability of the solution is also noted where the solution is clear, or not cloudy or hazy. Clarity may be determined by turbidity units that may be measured as Nephelometric Turbidity Units (NTU) as known in the art.

In one embodiment, the present application discloses a method of solubilizing resveratrol or pterostilbene, or a mixture of resveratrol and pterostilbene, in an aqueous media comprising: a) dissolving the resveratrol or pterostilbene, or a mixture thereof, and an emulsifying agent in a suitable solvent to form a homogeneous solution; b) evaporating the solvent to form a mixture of resveratrol or pterostilbene, or a mixture thereof, and the emulsifying agent; c) dissolving the resveratrol or pterostilbene mixture, or a mixture thereof, in the aqueous medium by stirring the mixture with a warm medium to form a stable emulsion of resveratrol or pterostilbene, or a mixture thereof, and emulsifying agent.

In one aspect of the above embodiments, the emulsifying agents are GRAS (Generally Recognized as Safe). In another aspect, the emulsifying agent has an HLB of greater than 9. In another aspect of each of the above, the emulsifying agent is TPGS (tocopherol polyethylene glycol succinate). In another aspect, the ratio of emulsifying agent to resveratrol or pterostilbene, or a mixture thereof, is in the range of 3:1 to 10:1. In another aspect of the above, the ratio of emulsifying agent to resveratrol or pterostilbene, or mixture thereof, is from 4:1 to 6:1. In another aspect, the ratio of emulsifying agent to resveratrol or pterostilbene, or a mixture thereof, is from 1:1 to 2:1. In another aspect, the resultant emulsion comprises a particle size of less than 250 nanometers. In yet another aspect, the resultant emulsion comprises a particle size of less than 100 nanometers, between 25 and 100 nanometers, less than 50 nanometers, or between 15 and 50 nanometers.

In another embodiment, there is provided a method for solubilizing resveratrol or pterostilbene from a co-crystal complex of resveratrol or pterostilbene and caffeine in aqueous media comprising: a) dissolving the resveratrol or pterostilbene complex, or a mixture thereof, and an emulsifying agent in a suitable solvent to form a homogeneous solution; b) evaporating the solvent to form a mixture of the resveratrol or pterostilbene complex, or a mixture thereof, and the emulsifying agent; and c) dissolving of the resveratrol or pterostilbene mixture, or a mixture thereof, in the aqueous medium by stirring the mixture with a warm medium to form a stable emulsion of resveratrol or pterostilbene, or a mixture thereof, and emulsifying agent.

In one aspect of the above, the warm medium is provided by heating the mixture above RT for a sufficient amount of time to form the stable emulsion. In another aspect, the warm medium is obtained by heating the mixture to about 30° C. to about 80° C., about 30° C. to about 70° C., about 30° C. to about 60° C., about 30° C. to about 50° C., or about 30° C. to about 40° C. In another aspect, the warm medium is obtained by heating the mixture to about 40° C. to about 70° C., or about 40° C. to about 60° C. In one aspect of the above embodiments, the emulsifying agents are GRAS (Generally Recognized as Safe). In another aspect, the emulsifying agents have an HLB of greater than 9. In another aspect, the emulsifying agent is TPGS (tocopherol polyethylene glycol succinate), TPGS-300 (D-alpha-tocopheryl polyethylene glycol 300 succinate), TPGS-500, TPGS-600, TPGS-750 and TPGS-1000, or a mixture thereof. In another aspect, the emulsifying agent is TPGS-M (tocopherol polyethylene glycol methyl ether succinate), TPGS-300-M (D-alpha-tocopheryl polyethylene glycol methyl ether 300 succinate), TPGS-500-M, TPGS-600-M, TPGS-750-M and TPGS-1000-M, or a mixture thereof. In another aspect, the emulsifying agent is selected from the group consisting of TPGS, TPGS-300, TPGS-500, TPGS-600, TPGS-750, TPGS-1000, TPGS-M, TPGS-300-M, TPGS-500-M, TPGS-600-M, TPGS-750-M and TPGS-1000-M, or a mixture thereof. In another aspect of the above, the ratio of emulsifying agent to resveratrol or pterostilbene, or a mixture thereof, is in the range of 3:1 to 10:1. In another aspect, the ratio of the emulsifying agent to resveratrol or pterostilbene, or a mixture thereof, is 1:1 to 3:1. In another aspect, the ratio of the emulsifying agent to resveratrol or pterostilbene, or a mixture thereof, is 4:1 to 5:1. In another aspect, the ratio of the emulsifying agent to resveratrol or pterostilbene, or a mixture thereof, is 5:1 to 8:1. In another aspect, the resultant emulsion has a particle size of less than 250 nanometers. In another aspect, the resultant emulsion comprises a particle size of less than 100 nanometers. In yet another aspect, the resultant emulsion comprises a particle size of between 25 and 100 nanometers. In another aspect, the resultant emulsion comprises a particle size of below 50 nanometers. In another aspect, the resultant emulsion comprises a particle size of between 15 and 50 nanometers. In one aspect of each of the above embodiments and aspects, the composition, formulation or emulsion comprises a mixture of resveratrol and pterostilbene. In one variation, the mixture of resveratrol to pterostilbene is in a ratio of about 95:5, 90:10, 85:15, 80:20, 75:25, 70:30, 65:35, 60:40, 55:45, 50:50, 45:55, 40:60, 35:65, 30:70, 25:75, 20:80, 15:85, 10:90 or 5:95.

In another embodiment of each of the above embodiments and aspect, there is provided a stable and homogeneous aqueous formulation or composition comprising the pterostilbene-caffeine co-crystal complex, a resveratrol-caffeine co-crystal complex and a mixture thereof in water is at a co-crystal complex:water (wt:wt) ratio of 10:90, 20:80, 30:70, 40:60, 50:50, 60:40, 70:30, 80:20, 90:10, 95:5 or more.

DETAILED DESCRIPTION OF THE INVENTION

We have discovered a methodology to solubilize resveratrol or pterostilbene, or a mixture thereof, such that it may be incorporated into aqueous based beverages readily at concentrations sufficient to provide doses appropriate for provision of the health benefits of resveratrol or pterostilbene, or a mixture thereof, for consumption. Such beverages include clear beverages, sodas such as Coke® or Pepsi®, fruit juices such as orange juice, apple juice, carbonated or non-carbonated water or beverages etc. . . . .

General procedures for preparation of nanoparticulate TPGS based formulations are found in Arbor Therapeutics, LLC Standard Operating Procedures; ART 001 Coarse Emulsion Preparation Rev. 1, and ART 003 Nicomp 380 ZLS Particle Size Analyses Rev. 1. Exceptions to these SOPs are noted as needed.

Abbreviations:

TPGS—D-a-Tocopheryl Polyethyleneglycol-1000-succinate, PSB—Pterostilbene; RVT—Resveratrol; IPA—Isopropanol; REM—resultant emulsion; %—percent of total solids; W/V—weight to volume; Recovery, %—percent of PSB recovered in resultant emulsion after sterile 0.22 μm filtration; mfg—manufacturing; ND—not determined; BDL—below detection limit; O/N—overnight.

List of Equipment Used:

| Description | Manufacturer | Model Number |
|---|---|---|
| 400 gram balance | Denver Instrument | SI-403 |
| 100 gram balance | Denver Instrument | APX-100 |
| Magnetic stirring plate | Barnstead Thermolyne, Cimarec | |
| Particle Sizer | Particle Sizing Systems | Nicomp ™ 380 ZLS |
| HPLC | Agilent | HP 1100 Series |

List of Materials Used:

| Reagent | Vendor | Part Number | Lot Number |
|---|---|---|---|
| D-a-Tocopheryl Polyethyleneglycol-1000-succinate | Isochem | NA | 1101040048 |
| Pterostilbene | ChromaDex. | ASB -00016996-100 | 00016996-1206 |
| Resveratrol | Sigma-Aldrich | R-5010 Sigma | NA |
| Distilled Water | Kroger Grocery | Distilled Water | NA |
| Sterile Filters, 0.22 µm, PES | Fisher Scientific | 50 mL 09-741-88 | NA |
|  |  | 150 mL 09-741-01 | NA |
|  |  | 500 mL 09-761-107 | NA |
| Cuvettes, polystyrene 4.5 mL | Fisher Scientific | 14 955 125 | NA |
| Powerade, Lemon Lime | Powerade |  | DEC3013CCB3B, 13:37 CT931 |
| Lifewater, strawberry dragonfruit | SOBE |  | AUG2613, 0115DL022234 |
| Minute Maid, Pink lemonade | Minute Maid |  | LTF7W4P, RTKS4LN |
| Welch's Tropical Carrot | Welch's |  | NE12K16 17 04:46 C |
| Vitamin water, acai-blueberry-pomegranate | GLACEAU |  | SEP0913CCC1A, 10:21 CT931 |
| Perform 02, G series | GATORADE |  | OCT3013CT564, 1108TL020235 |
| Pluronic 31R1 Poly (Propylene glycol)-block-Poly (Ethylene glycol)-block-Poly (Propylene glycol) PPG-PEG-PPG | Sigma-Aldrich | 1001438194 435503 | MKBC5295V |
| Pluronic 17R4 Poly (Propylene glycol)-block-Poly (Ethylene glycol)-block-Poly (Propylene glycol) PPG-PEG-PPG | Sigma-Aldrich | 1001452647 435481 | 02011BJV |
| Pluronic L-64 Poly (Propylene glycol)-block-Poly (Ethylene glycol)-block-Poly (Propylene glycol) PPG-PEG-PPG | Sigma-Aldrich | 1001442463 435449 | MKBF4936V |
| Pterostilbene and Caffeine Co-Crystal | Chromadex | 00016988 | 00016988-0204 |
| Caffeine, 99% | Alfa Aesar | A10431 | B06Y038 |
| Cremophor ® ELP | Sigma-Aldrich | 30906 | BCBH0387V |

For the preparation of TPGS-750-M and related compounds, see "TPGS-750-M: A Second-Generation Amphiphile for Metal-Catalyzed Cross-Couplings in Water at Room Temperature" Lipshutz, B. H. et al. *J. Org. Chem.* 2011, 76, 4379-4391, and Sigma Aldrich. The following experimental description detailed for the analysis of pterostilbene is also performed similarly with resveratrol, and mixtures thereof. The analytical results for resveratrol compositions are similar to those obtained for pterostilbene, and a mixture thereof.

Analytical Quantitation of Pterostilbene (PSB) or Resveratrol (RVT).

Quantitation of pterostilbene in concentrated TPGS emulsions employs the analytical method Pterostilbene.M. or Resveratrol.M. Phenomenex 4.6×50 mm Luna 5µ C18(2) 100 A, part number 00B-4252-E0 column, mobile phase: isocratic 40/60 acetonitrile/0.01 M $H_3PO_4$ water for 7 minutes followed by a column wash and re-equilibration, flow rate: 1.5 mL/minute, detection: 254 nm, column temperature: 40° C., and injection volume: 5 µL. Sample preparation is a 1:10 dilution with isopropanol. Pterostilbene elutes at 4.5 minutes. A calibration curve/response linearity was prepared using 0.1, 0.25, 0.5, 1.0 and 2.5 mg/mL solutions. Response is linear with $R^2$ of 0.9999. Since the target concentration of pterostilbene in consumer products is expected to be about 0.08 mg/mL (50-100 mg/drink serving), the sensitivity of the method was increased by changing the detection wavelength to 310 nm, the absorbance max of pterostilbene. Quantitation of resveratrol and mixture thereof may be performed as above.

Quantitation of pterostilbene in consumer products employs the analytical method Pterostilbene 310 nm.M. Method: Phenomenex 4.6×50 mm Luna 5µ C18(2) 100 A, part number 00B-4252-E0 column, mobile phase: isocratic 40/60 acetonitrile/0.01 M $H_3PO_4$ water for 7 minutes followed by a column wash and re-equilibration, flow rate: 1.5 mL/minute, detection: 310 nm, column temperature: 40° C., and injection volume: 5 µL. Sample preparation is a 1:1 dilution with isopropanol. Pterostilbene elutes at 4.5 minutes. A calibration curve/response linearity was prepared using 0.01, 0.025, 0.05, and 0.1 mg/mL solutions. The response is linear with an $R^2$ of 0.9997. Quantitation of resveratrol, or mixture thereof may also employ as above.

Quantitation of pterostilbene and caffeine in one method requires a detection wavelength at which both compounds have UV adsorbance and a mobile phase composition change to retain caffeine slightly in the analysis. Quantitation of pterostilbene and caffeine in concentrated TPGS emulsions employs the analytical method Pterostilbene 280.M. Method: Phenomenex 4.6×50 mm Luna 5µ C18(2) 100 A, part number 00B-4252-E0 column, mobile phase: 100% 0.01 M $H_3PO_4$ water for 0.5 minutes, 100 to 60% 0.01 M $H_3PO_4$ water/40% acetonitrile from 0.5 to 2 minutes then hold for 5 minutes 40/60 acetonitrile/0.01 M $H_3PO_4$ water followed by a column wash and re-equilibration, flow rate: 1.5 mL/minute, detection: 280 nm, column temperature: 40° C., and injection volume: 1 µL. Sample preparation is a 1:10 dilution with isopropanol. Caffeine elutes at 2.4 minutes and pterostilbene elutes at 7.1 minutes. Quantitation of resveratrol and caffeine, and mixture thereof, may use the above method.

Example 1. Preparation of 5 mg/mL PSB/TPGS, or RVT/TPGS Emulsion

Emulsion preparation: 5.008 g of TPGS was added to 100 mL of distilled water and mixed on magnetic stirring plate for 1 hr. 1 g of PSB was dissolved in 1.2 mL of 95% ethanol. 0.6 mL of ethanol solution of PSB was added slowly to 100 mL of clear TPGS solution during mixing. The mixture stirred for 2 hr at RT. Upon clearing, the emulsion was filtered through 0.22 µm filter, and particle size and PSB content of emulsion noted in Table 1.

TABLE 1

Particle size, PSB content, and particle stability of resultant emulsion.

| Manufacturing Date | Lot# | Particle size by intensity, nm | PSB Content, mg/mL | Recovery, % | Formulation Stability Days past mfg | Particle size nm |
|---|---|---|---|---|---|---|
| 11 Jun. 2013 | 005.20.3 | 23.5 | 4.08 | 81.6 | 14 | 21.7 |

HPLC Analysis.

"Pterostilbene.M." method was used for determination of PSB content. PSB content in resultant emulsion determined by HPLC was 4.08 mg/mL. Data indicate that 81.6% of the PSB used for preparation of this formulation was incorporated into TPGS particles (Table 1). Analysis of RVT provides similar results with PSB above.

Particle Size Analysis and Stability.

The resultant emulsion was stable. Table 1 shows that particle size did not increase over 14 days of monitoring. Particle size for RVT are similar to PSB.

Example 2. Preparation of 10 mg/mL PSB/TPGS Emulsion 5.004 g of TPGS and 1.003 g of PSB were weighed and placed in 400 mL beaker. 9 mL of 95% ethanol were added to the solids, and the beaker containing ethanol mixture of TPGS/PSB was placed in the water bath, and incubated at 60° C. for 20 min until clear. The beaker with ethanol TPGS/PSB solution was placed into vacuum oven O/N.

Emulsion preparation: The beaker was removed from vacuum oven and 100 mL of distilled water preheated to 60° C. was added to the highly viscous clear film of TPGS/PBS mixture, the beaker was placed in 60° C. water bath and total mixture was incubated for 30 min to dissolve. The water TPGS/PBS mixture was mixed on magnetic stirring plate for 2 hrs at RT. Upon clearing of the mixture, the emulsion was filtered through 0.22 µm filter, and particle size and PSB content of the resultant emulsion were determined (Table 2).

TABLE 2

Particle size, PSB content, and particle stability of resultant emulsion.

| Manufacturing Date | Lot# | Particle size by intensity, nm | PSB Content, mg/mL | Recovery, % | Formulation Stability Days past mfg | Particle size nm |
|---|---|---|---|---|---|---|
| 12 Jun. 2013 | 005.21.4 | 26.1 | 10.57 | 105.6 | 40 | 25.9 |

HPLC Analysis.

"Pterostilbene. 310 nm.M." method was used for determination of PSB content. PSB content in resultant emulsion determined by HPLC was 10.57 mg/mL. Data indicate that 105.6% of the PSB used for preparation of this formulation was incorporated into TPGS particles (Table 2). An incorporation value above 100% could result because of water evaporation during 30 min of incubation at 60° C.

Particle Size Analysis and Stability.

The resultant emulsion was stable. It can be seen in Table 2 that particle size did not significantly change over 40 days of monitoring.

Example 3. Dilution of PSB/TPGS Emulsion into Distilled Water

Procedure 1:

PSB/TPGS/Water solution preparation: 170 µl of TPGS/PSB emulsion (lot#005.21.4) was added to 21 mL of Distilled Water. The water solution of PSB/TPGS emulsion was briefly mixed and stored for 3 days at RT. 3 Days later 0.6 mL aliquot of PSB/TPGS/Water solution was diluted 1:1 with IPA, and HPLC analysis of PSB in Table 3a.

TABLE 3a

PSB content of resultant solution.

| Preparation Date | HPLC Date | PSB content Calculated PSB, mg/mL | HPLC, mg/mL | Recovery, % | Days past preparation |
|---|---|---|---|---|---|
| 14-Jun-13 | | 0.086 | ND | N/A | 0 |
| | 17-Jun-13 | 0.086 | 0.083 | 97.00 | 3 |

HPLC Analysis.

"Pterostilbene 310 nm.M" method was used for determination of PSB content. Table 3a shows that after 3 days of storage at RT the PSB content in resultant solution determined by HPLC was similar to calculated amount of PSB added to the beverage. Data shows that formulated PSB is stable in water.

Procedure 2:

PSB/TPGS/Water solution preparation: 170 μl of TPGS/PSB emulsion (lot#005.21.4) was added to 21 mL of Distilled Water. The solution of PSB/TPGS emulsion was mixed and stored for 3 and/or 11 days at RT. 3 or 11 Days later 0.6 mL aliquot of PSB/TPGS/Water solution was diluted 1:1 with IPA, filtered through 0.22 μm filter, and HPLC analysis of PSB content was performed (Table 3b).

TABLE 3b

PSB content and Stability of resultant solution.

| Preparation Date | HPLC Date | Calculated PSB, mg/mL | HPLC, mg/mL | Recovery, % | Days past preparation |
|---|---|---|---|---|---|
| 14-Jun-13 |  | 0.086 | ND | N/A | 0 |
|  | 17-Jun-13 | 0.086 | 0.082 | 95.83 | 3 |
|  | 25-Jun-13 | 0.086 | 0.084 | 98.17 | 11 |

HPLC Analysis.

"Pterostilbene 310 nm.M" method was used for determination of PSB content. Table 3b shows that after 11 days of storage at RT the PSB content in resultant solution determined by HPLC was similar to calculated amount of PSB added to the water. Data shows high stability of formulated PSB in water.

Procedure 3:

PSB/TPGS/Water solution preparation: 170 μl of TPGS/PSB emulsion (lot#005.21.4) was added to 21 mL of Distilled Water. The water solution of PSB/TPGS emulsion was briefly mixed and stored for 3 days at RT. 3 Days later 1.0 mL aliquot of PSB/TPGS/Water solution was filtered through 0.22 μm filter, diluted 1:1 with IPA, and HPLC analysis of PSB content was performed (Table 3c).

TABLE 3c

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 |  | 0.086 | ND | N/A | 0 |
|  | 17-Jun-13 | 0.086 | 0.073 | 85.31 | 3 |

HPLC Analysis.

"Pterostilbene 310 nm.M" method was used for determination of PSB content. Table 3c shows that PSB content of the water/PSB/TPGS emulsion when first filtered and then diluted with IPA was significantly lower compared to unfiltered (Procedure 1) and/or dilution with IPA first and then filtered (Procedure 2) solutions. Considering that no degradation of PSB or precipitate was observed in the water, the data suggest loss of some material on the filter when not diluted with IPA. Procedure 1 and 2 yielded similar PSB content.

Particle Size Analysis and Stability.

PSB/TPGS/Water solution preparation: 170 μl of PSB/TPGS emulsion (lot#005.21.4) was added to 21 mL of Distilled Water. The water solution of PSB/TPGS emulsion was mixed and stored for 0, 2, and 6 days at RT. 0, 2, and/or 6 days later 0.3 mL of PSB/TPGS/Water solution was added to the cuvette containing 2.2 mL of distilled water and particle size was measured. To obtain baseline for distilled water 0.3 mL of distilled water were added to cuvette containing 2.2 mL of distilled water. Particle size analysis is presented in the Table 3d.

TABLE 3d

Particle size and stability.

| Preparation Date | Material | Particle size by intensity, nm | Days past preparation |
|---|---|---|---|
| 19-Jun-13 | Water | N/A | 0 |
| 19-Jun-13 | Water plus Lot# 005.21.4 | 36.6 | 0 |
| 21-Jun-13 | Water plus Lot# 005.21.4 | 37.7 | 2 |
| 25-Jun-13 | Water plus Lot# 005.21.4 | 38.0 | 6 |

Particle size did not change over 6 days of storage at RT. Dilution in water does not impair emulsion stability. Data show chemical and particle stability of formulated PSB.

Example 4. Preparation of PSB/TPGS/Reb A Emulsion 100 mg of Reb A was added directly to 5 mL of PSB/TPGS emulsion lot#005.21.4 and mixed on magnetic stirring plate at RT until clear (~30 min). Upon clearing of the mixture, the emulsion was filtered through 0.22 μm filter, and particle size and PSB content of the emulsion determined (Table 4).

TABLE 4

Particle size, PSB content, and particle stability of resultant emulsion.

| Manufacturing Date | Lot# | Particle size by intensity, nm | PSB Content, mg/mL | PSB Recovery, % | Formulation Stability Days past mfg | Formulation Stability Particle size nm |
|---|---|---|---|---|---|---|
| 14 Jun. 2013 | 005.21.5 | 16.2 | 9.60 | 90.8 | 4 | 16.1 |

HPLC Analysis.

"Pterostilbene.M." method was used for determination of PSB content. PSB content in resultant emulsion determined by HPLC was 9.6 mg/mL. The data indicate that 90.8% of the PSB determined in emulsion lot #005.21.4 was recovered in Reb A containing emulsion (Table 4). Direct filtration of the aqueous PSB/TPGS emulsion without first dilution in IPA causes some loss to the filter by adsorption onto the filter membrane.

Particle Size Analysis and Stability.

The particle size of the Reb A containing emulsion was significantly smaller than the emulsion with PSB and TPGS only. The resultant emulsion was stable. As seen in Table 4 particle size did not change over 4 days of monitoring.

Example 5. Dilution of PSB/TPGS/Reb A Emulsion in Distilled Water

Procedure 1:

PSB/TPGS/Reb A water solution preparation: 170 µl of PSB/TPGS/Reb A emulsion (lot#005.21.5) was added to 20 mL of distilled water. The water solution of PSB/TPGS/Reb A emulsion (lot#005.21.5) was mixed and stored for 3 days at RT. 3 Days later 0.6 mL aliquot of PSB/TPGS/Reb A/Water solution was diluted 1:1 with IPA, and HPLC analysis of PSB content was performed (Table 5a).

TABLE 5a

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.082 | ND | N/A | 0 |
| | 17-Jun-13 | 0.082 | 0.081 | 99.26 | 3 |

HPLC Analysis. "Pterostilbene 310 nm.M" method was used for determination of PSB content. Table 5a shows that after 3 days of storage at RT PSB content of resultant solution determined by HPLC was similar to calculated amount of PSB added to the water. Data shows that TPGS/Reb A formulated PSB is stable in water.

Procedure 2:

PSB/TPGS/Reb A water solution preparation: 170 µl of PSB/TPGS/Reb A emulsion (lot#005.21.5) was added to 20 mL of distilled water. The solution of PSB/TPGS/Reb A emulsion was mixed and stored for 3 or 11 days at RT. 3 or 11 Days later 0.6 mL aliquot of PSB/TPGS/Reb A water solution was diluted 1:1 with IPA, filtered through 0.22 µm filter, and HPLC analysis of PSB content (Table 5b).

TABLE 5b

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.082 | ND | N/A | 0 |
| | 17-Jun-13 | 0.082 | 0.081 | 99.26 | 3 |
| | 25-Jun-13 | 0.082 | 0.083 | 101.72 | 11 |

HPLC Analysis.

"Pterostilbene 310 nm.M" method was used for determination of PSB content. Table 5b shows that after 11 days of storage at RT PSB content in resultant solution determined by HPLC was similar to calculated amount of PSB added to the aqueous medium. Data suggest that TPGS/Reb A formulated PSB is stable in water.

Procedure 3:

PSB/TPGS/Reb A water solution preparation: 170 µl of PSB/TPGS/Reb A emulsion (lot#005.21.5) was added to 20 mL of distilled water. Water solution of PSB/TPGS/Reb A emulsion was briefly mixed and stored for 3 days at RT. 3 Days later 1.0 mL aliquot of PSB/TPGS/Reb A/Water solution was filtered through 0.22 µm filter, diluted 1:1 with IPA, and HPLC analysis of PSB content was performed (Table 5c).

TABLE 5c

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.082 | ND | N/A | 0 |
| | 17-Jun-13 | 0.082 | 0.068 | 83.33 | 3 |

HPLC Analysis.

"Pterostilbene 310 nm.M" method was used for determination of PSB content. Table 5c shows that PSB content of the emulsion mixture directly filtered and then diluted with IPA was significantly lower compared to unfiltered (Procedure 1) and/or diluted with IPA first and then filtered (Procedure 2) solutions. No degradation of PSB or precipitate was observed in the water, the data rather suggest the loss of some material on the filter when the emulsion preparation is not diluted with IPA. Procedure 1 and 2 yielded similar PSB content.

Particle Size Analysis and Stability.

PSB/TPGS/Reb A/Water solution preparation: 170 µl of PSB/TPGS/Reb A emulsion (lot#005.21.5) was added to 20 mL of distilled water. Water solution of PSB/TPGS/Reb A emulsion was briefly mixed and stored for 6 days at RT. Immediately after preparation and/or 6 days later 0.3 mL of PSB/TPGS/Reb A/Water solution was added to the cuvette containing 2.2 mL of distilled water and particle size was measured. To obtain baseline for distilled water 0.3 mL of distilled water were added to cuvette containing 2.2 mL of distilled water. See Table 5d.

TABLE 5d

Particle size and stability.

| Preparation Date | Material | Particle size by intensity, nm | Days past preparation |
| --- | --- | --- | --- |
| 19-Jun-13 | Water | N/A | 0 |
| 19-Jun-13 | Water plus Lot# 005.21.5 | 20.9 | 0 |
| 25-Jun-13 | Water plus Lot# 005.21.5 | 21.7 | 6 |

The particle size did not change over 6 days of storage at RT. Data suggest that dilution in water does not impair PSB/TPGS/Reb A emulsion (lot#005.21.5) stability under these conditions (Table 5d). Data shows chemical and particle stability of PSB in water.

Example 6. Preparation of PSB/TPGS/PowerAde Solution

TABLE 6a

Formulation composition.

| | mg per 22 ml | | |
| --- | --- | --- | --- |
| Date | TPGS | PSB | Powerade |
| 14-Jun-13 | 8.5 | 1.7 | 22 ml |

Procedure 1:

PSB/TPGS/PowerAde solution preparation: 170 μl of TPGS/PSB emulsion (lot#005.21.4) was added to 22 mL of PowerAde beverage. PowerAde solution of PSB/TPGS emulsion was mixed and stored for 3 days at RT. 3 Days later 0.6 mL aliquot of PSB/TPGS/PowerAde solution was diluted 1:1 with IPA, and HPLC analysis of PSB content was performed (Table 6b).

TABLE 6b

PSB content of resultant solution. Stability.

| | | PSB content | | | |
| --- | --- | --- | --- | --- | --- |
| Preparation Date | HPLC Date | Calculated PSB, mg/ml | HPLC, mg/ml | Recovery, % | Days past preparation |
| 14-Jun-13 | | 0.082 | ND | N/A | 0 |
| | 17-Jun-13 | 0.082 | 0.079 | 96.72 | 3 |

HPLC Analysis.

"Pterostilbene 310 nm.M" method was used for determination of PSB content. Table 6b that after 3 days of storage at RT PSB content in resultant solution determined by HPLC was similar to calculated amount of PSB added to the beverage. Data suggest that TPGS formulated PSB is stable in PowerAde beverage.

Procedure 2:

PSB/TPGS/PowerAde solution preparation: 170 μl of PSB/TPGS emulsion (lot#005.21.4) was added to 22 mL of PowerAde beverage. PSB/TPGS/PowerAde solution was briefly mixed and stored for 3 or 11 days at RT. 3 or 11 Days later 0.6 mL aliquot of PSB/TPGS/PowerAde solution was diluted 1:1 with IPA, filtered through 0.22 μm filter, and HPLC analysis of PSB content was performed (Table 6c).

TABLE 6c

PSB content of resultant solution.

| | | PSB content | | | |
| --- | --- | --- | --- | --- | --- |
| Preparation Date | HPLC Date | Calculated PSB, mg/mL | HPLC, mg/mL | Recovery, % | Days past preparation |
| 14-Jun-13 | | 0.082 | ND | N/A | 0 |
| | 17-Jun-13 | 0.082 | 0.079 | 96.72 | 3 |
| | 25-Jun-13 | 0.082 | 0.081 | 99.17 | 11 |

HPLC Analysis.

"Pterostilbene 310 nm.M" method was used for determination of PSB content. Table 6c shows that after 11 days of storage at RT PSB content in the resultant solution determined by HPLC was similar to calculated amount of PSB added to the beverage. Data shows that TPGS formulated PSB is stable in PowerAde beverage.

Procedure 3:

PSB/TPGS/PowerAde solution preparation: 170 μl of PSB/TPGS emulsion (lot#005.21.4) was added to 22 mL of PowerAde beverage. PSB/TPGS/PowerAde solution was briefly mixed and stored for 3 days at RT. 3 Days later 0.6 mL aliquot of PSB/TPGS/PowerAde solution was filtered through 0.22 μm filter, diluted 1:1 with IPA, and HPLC analysis of PSB content was performed (Table 6d).

TABLE 6d

PSB content of resultant solution.

| | | PSB content | | | |
| --- | --- | --- | --- | --- | --- |
| Preparation Date | HPLC Date | Calculated PSB, mg/mL | HPLC, mg/mL | Recovery, % | Days past preparation |
| 14-Jun-13 | | 0.082 | ND | N/A | 0 |
| | 17-Jun-13 | 0.082 | 0.062 | 75.91 | 3 |

HPLC Analysis.

"Pterostilbene 310 nm.M" method was used for determination of PSB content. Table 6d (recovery %) shows that PSB content of directly filtered PSB/TPGS/PowerAde solution and then dilution with IPA was significantly lower compared to unfiltered (Procedure 1) and/or diluted with IPA and then filtered (Procedure 2) solutions. PSB recovery in filtered PowerAde solution of formulated PSB was significantly lower compared to that of filtered PSB/TPGS water solution (examples 3 and 5). Data shows that part of the formulated PSB was bound to the PowerAde coarse matrix and was retained on the filter during filtration. Dilution of PSB/TPGS/PowerAde solution with IPA prior to filtration releases PSB from the PowerAde matrix and prevents its filter retention.

Particle Size Analysis and Stability.

PSB/TPGS/PowerAde solution preparation: 170 μl of PSB/TPGS emulsion (lot#005.21.4) was added to 22 mL of PowerAde beverage. PSB/TPGS/PowerAde solution was mixed and stored for 2 and 6 days at RT.

To avoid contribution of coarse beverage matrix to particle size measurement, the beverage was centrifuged at 13,000 rpm for 15 min in an eppendorf centrifuge. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. See Table 6e.

TABLE 6e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | Powerade | 609.9 | 0 |
| 19-Jun-13 | Powerade plus Lot# 005.21.4 | 40.7 | 0 |
| 21-Jun-13 | Powerade plus Lot# 005.21.4 | 39.6 | 2 |
| 25-Jun-13 | Powerade plus Lot# 005.21.4 | 41.6 | 6 |

There was 4 nm initial increase of the particle size of the TPGS/PSB emulsion upon dilution in Powerade beverage, the particle size did not change over next six days. Absence of further particle size change suggests stability of formulated PSB in Powerade beverage. Data obtained indicate chemical and particle stability of formulated PSB in Powerade beverage and suggest 100% of PSB consumption with the beverage.

Example 7. Preparation of PSB/TPGS/LifeWater Solution

TABLE 7a

Formulation composition.

| | mg per 21 mL | | |
|---|---|---|---|
| Date | TPGS | PSB | LifeWater |
| 14-Jun-13 | 8.5 | 1.7 | 21 mL |

Procedure 1:

PSB/TPGS/LifeWater solution preparation: 170 μl of TPGS/PSB emulsion (lot#005.21.4) was added to 21 mL of LifeWater beverage. LifeWater solution of PSB/TPGS emulsion was mixed and stored for 3 days at RT. 3 Days later 0.6 mL aliquot of PSB/TPGS/LifeWater solution was diluted 1:1 with IPA, and HPLC analysis of PSB in Table 7b.

TABLE 7b

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.082 | 95.83 | 3 |

HPLC Analysis.

"Pterostilbene 310 nm.M" method was used for determination of PSB content. Table 7b shows that after 3 days of storage at RT PSB content in resultant solution determined by HPLC was similar to calculated amount of PSB added to the beverage. The data shows that TPGS formulated PSB is stable in LifeWater beverage.

Procedure 2:

PSB/TPGS/LifeWater solution preparation: 170 μl of PSB/TPGS emulsion (lot#005.21.4) was added to 21 mL of LifeWater beverage. PSB/TPGS/LifeWater solution was briefly mixed and stored for 3 or 11 days at RT. 3 or 11 Days later 0.6 mL aliquot of PSB/TPGS/LifeWater solution was diluted 1:1 with IPA, filtered through 0.22 μm filter, and HPLC analysis of PSB content was performed (Table 7c).

TABLE 7c

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.077 | 89.99 | 3 |
| | 25-Jun-13 | 0.086 | 0.091 | 106.35 | 11 |

HPLC Analysis.

"Pterostilbene 310 nm.M" method was used for determination of PSB content. Table 7c shows that after 11 days of storage at RT PSB content in resultant solution determined by HPLC was similar to calculated amount of PSB added to the beverage. Data suggest that TPGS formulated PSB is stable in LifeWater beverage.

Procedure 3:

PSB/TPGS/LifeWater solution preparation: 170 μl of PSB/TPGS emulsion (lot#005.21.4) was added to 21 mL of LifeWater beverage. PSB/TPGS/LifeWater solution was briefly mixed and stored for 3 days at RT. 3 Days later 0.6 mL aliquot of PSB/TPGS/LifeWater solution was filtered through 0.22 μm filter, diluted 1:1 with IPA, and HPLC analysis of PSB content was performed (Table 7d).

TABLE 7d

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.069 | 80.64 | 3 |

HPLC Analysis.

"Pterostilbene 310 nm.M" method was used for determination of PSB content. Table 7d (recovery %) shows that PSB content of directly filtered PSB/TPGS/LifeWater solution and dilution with IPA was lower compared to unfiltered (Procedure 1) and/or diluted with IPA and then filtered (Procedure 2) solutions. PSB recovery in filtered LifeWater solution of formulated PSB was similar to that of filtered PSB/TPGS water solution (examples 3 and 5). Data shows no significant binding of formulated PSB to LifeWater matrix.

Particle Size Analysis and Stability.

PSB/TPGS/LifeWater solution preparation: 170 μl of PSB/TPGS emulsion (lot#005.21.4) was added to 21 mL of LifeWater beverage. PSB/TPGS/LifeWater solution was briefly mixed and stored for 2 and 6 days at RT. The beverage was centrifuged at 13,000 rpm for 15 min in an eppendorf centrifuge. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. See Table 7e.

TABLE 7e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | LifeWater | 376.9 | 0 |
| 19-Jun-13 | LifeWater plus Lot# 005.21.4 | 39.2 | 0 |
| 21-Jun-13 | LifeWater plus Lot# 005.21.4 | 37.9 | 2 |
| 25-Jun-13 | LifeWater plus Lot# 005.21.4 | 38.9 | 6 |

Although, there was 3 nm initial increase of the particle size of the TPGS/PSB emulsion upon dilution in LifeWater beverage, the particle size did not change over next six days of monitoring. Data shows that contribution of beverage only particles into final particle size of the mixture was not significant. Absence of further particle size change suggests stability of formulated PSB in LifeWater beverage. Data indicate chemical and particle stability of formulated PSB in LifeWater beverage and show 100% of PSB consumption with the beverage.

Example 8. Preparation of PSB/TPGS/Minute Maid Solution

TABLE 8a

Formulation composition.

| | mg per 22 mL | | |
|---|---|---|---|
| Date | TPGS | PSB | Minute Maid |
| 14-Jun-13 | 8.5 | 1.7 | 22 mL |

Procedure 1:

PSB/TPGS/Minute Maid solution preparation: 170 μl of TPGS/PSB emulsion (lot#005.21.4) was added to 22 mL of Minute Maid beverage. Minute Maid solution of PSB/TPGS emulsion was briefly mixed and stored for 3 days at RT. 3 Days later 0.6 mL aliquot of PSB/TPGS/Minute Maid solution was diluted 1:1 with IPA. See Table 8b.

TABLE 8b

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.082 | ND | N/A | 0 |
| | 17-Jun-13 | 0.082 | 0.075 | 91.82 | 3 |

HPLC Analysis. "Pterostilbene 310 nm.M" method was used for determination of PSB content. Table 8b shows that after 3 days of storage at RT PSB content was determined by HPLC was similar to calculated amount of PSB added to the beverage. Data suggest that TPGS formulated PSB is stable in Minute Maid beverage.

Procedure 2:

PSB/TPGS/Minute Maid solution preparation: 170 μl of PSB/TPGS emulsion (lot#005.21.4) was added to 22 mL of Minute Maid beverage. PSB/TPGS/Minute Maid solution was briefly mixed and stored for 3 or 11 days at room temperature (RT). 3 or 11 Days later 0.6 mL aliquot of PSB/TPGS/Minute Maid solution was diluted 1:1 with IPA, filtered through 0.22 μm filter. HPLC analysis of PSB content in Table 8c.

TABLE 8c

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.082 | ND | N/A | 0 |
| | 17-Jun-13 | 0.082 | 0.077 | 94.27 | 3 |
| | 25-Jun-13 | 0.082 | 0.089 | 108.97 | 11 |

HPLC Analysis.

"Pterostilbene 310 nm.M" method was used for determination of PSB content. Table 8c shows that after 11 days of storage at RT PSB content in resultant solution determined by HPLC was similar to calculated amount of PSB added to the beverage. Data suggest that TPGS formulated PSB is stable in Minute Maid beverage.

Procedure 3:

PSB/TPGS/Minute Maid solution preparation: 170 μl of PSB/TPGS emulsion (lot#005.21.4) was added to 22 mL of Minute Maid beverage. PSB/TPGS/Minute Maid solution was briefly mixed and stored for 3 days at RT. 3 Days later 0.6 mL aliquot of PSB/TPGS/Minute Maid solution was filtered through 0.22 μm filter, diluted 1:1 with IPA and HPLC analysis of PSB content was performed (Table 8d).

TABLE 8d

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.082 | ND | N/A | 0 |
| | 17-Jun-13 | 0.082 | 0.056 | 68.56 | 3 |

HPLC Analysis.

"Pterostilbene 310 nm.M" method was used for determination of PSB content. Table 8d (recovery %) shows that PSB content of directly filtered PSB/TPGS/Minute Maid solution and then dilution with IPA was significantly lower compared to unfiltered (Procedure 1) and/or diluted with IPA and then filtered (Procedure 2) solutions. PSB recovery in filtered Minute Maid solution of formulated PSB was notably lower compared to that of filtered water PSB/TPGS solution (examples 3 and 5). Data suggest that a substantial portion of formulated PSB was bound to the Minute Maid coarse matrix and was retained on the filter during filtration. Dilution of PSB/TPGS/Minute Maid solution with IPA prior to filtration releases PSB from the Minute Maid matrix and prevents its filter retention.

Particle Size Analysis and Stability.

PSB/TPGS/Minute Maid solution preparation: 170 μl of PSB/TPGS emulsion (lot#005.21.4) was added to 22 mL of Minute Maid beverage. PSB/TPGS/Minute Maid solution was briefly mixed and stored for 2 and 6 days at RT. The beverage was centrifuged at 13,000 rpm for 15 min in an eppendorf centrifuge. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. See Table 8e.

TABLE 8e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | Minute Maid | 392.2 | 0 |
| 19-Jun-13 | Minute Maid plus Lot# 005.21.4 | 47.9 | 0 |
| 21-Jun-13 | Minute Maid plus Lot# 005.21.4 | 47.3 | 2 |
| 25-Jun-13 | Minute Maid plus Lot# 005.21.4 | 48.4 | 6 |

There was a 11 nm increase of the particle size of formulated PSB upon dilution in Minute Maid beverage. The particle size did not change over the next six days of monitoring. These results suggest significant contribution of beverage only particles into final particle size of the mixture. The light scattering data are in agreement with HPLC data demonstrating substantial binding of formulated PSB to Minute Maid coarse matrix. Absence of further particle size change suggests stability of formulation. Data indicate chemical and particle stability of formulated PSB in Minute Maid beverage and suggest 100% of PSB consumption with beverage.

Example 9. Preparation of PSB/TPGS/Welch's Tropical Carrot Solution

TABLE 9a

Formulation composition.

| | mg per 20 mL | | |
|---|---|---|---|
| Date | TPGS | PSB | Welch's Tropical Carrot |
| 14-Jun-13 | 8.5 | 1.7 | 20 mL |

Procedure 1:

PSB/TPGS/Welch's Tropical Carrot solution preparation: 170 μl of TPGS/PSB emulsion (lot#005.21.4) was added to 20 mL of Welch's Tropical Carrot beverage. Welch's Tropical Carrot solution of PSB/TPGS emulsion was briefly mixed and stored for 3 days at RT. 3 Days later 0.6 mL aliquot of PSB/TPGS/Welch's Tropical Carrot solution was diluted 1:1 with IPA. HPLC analysis of PSB content was not performed due to precipitation of the matrix (Table 9b).

TABLE 9b

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.090 | ND | N/A | 0 |
| | 17-Jun-13 | 0.090 | N/A | N/A | 3 |

Procedure 2:

PSB/TPGS/Welch's Tropical Carrot solution preparation: 170 μl of PSB/TPGS emulsion (lot#005.21.4) was added to 20 mL of Welch's Tropical Carrot beverage. PSB/TPGS/Welch's Tropical Carrot solution was briefly mixed and stored for 3 or 11 days at RT. 3 or 11 Days later 0.6 mL aliquot of PSB/TPGS/Welch's Tropical Carrot solution was diluted 1:1 with IPA, filtered through 0.22 μm filter, and HPLC analysis of PSB content was performed (Table 9c).

TABLE 9c

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.082 | ND | N/A | 0 |
| | 17-Jun-13 | 0.090 | 0.085 | 94.61 | 3 |
| | 25-Jun-13 | 0.090 | 0.089 | 99.06 | 11 |

HPLC Analysis.

"Pterostilbene 310 nm.M" method was used for determination of PSB content. Table 9c shows that after 11 days of storage at RT PSB content of resultant solution determined by HPLC was similar to calculated amount of PSB added to the beverage. Data shows that TPGS formulated PSB is stable in Welch's Tropical Carrot beverage.

Procedure 3:

PSB/TPGS/Welch's Tropical Carrot solution preparation: 170 µl of PSB/TPGS emulsion (lot#005.21.4) was added to 20 mL of Welch's Tropical Carrot beverage. PSB/TPGS/Welch's Tropical Carrot solution was briefly mixed and stored for 3 days at RT. 3 Days later 0.6 mL aliquot of PSB/TPGS/Welch's Tropical Carrot solution was filtered through 0.22 µm filter, diluted 1:1 with IPA, and HPLC analysis of PSB content was performed (Table 9d).

TABLE 9d

PSB content of resultant solution.

| | | PSB content | | | |
|---|---|---|---|---|---|
| Preparation Date | HPLC Date | Calculated PSB, mg/mL | HPLC, mg/mL | Recovery, % | Days past preparation |
| 14-Jun-13 | | 0.090 | ND | N/A | 0 |
| | 17-Jun-13 | 0.090 | 0.034 | 37.84 | 3 |

HPLC Analysis.

"Pterostilbene 310 nm.M" method was used for determination of PSB content. Table 9d (recovery %) shows that PSB content of directly filtered PSB/TPGS/Welch's Tropical Carrot solution and then dilution with IPA was dramatically lower compared to unfiltered (Procedure 1) and/or diluted with IPA and then filtered (Procedure 2) solutions. PSB recovery in filtered Welch's Tropical Carrot solution of formulated PSB was more than twice lower compared to that of filtered PSB/TPGS water solution (examples 3 and 5). Data suggest that a major portion of formulated PSB was bound to Welch's Tropical Carrot coarse matrix and was retained on the filter during filtration. Dilution of PSB/TPGS/Welch's Tropical Carrot solution with IPA prior to filtration releases PSB from Welch's Tropical Carrot matrix and prevents its filter retention. Welch's Tropical Carrot beverage has precipitation of coarse matrix in its original bottle and written manufacturer instruction "Shake well".

Particle Size Analysis and Stability.

PSB/TPGS/Welch's Tropical Carrot solution preparation: 170 µl of PSB/TPGS emulsion (lot#005.21.4) was added to 20 mL of Welch's Tropical Carrot beverage. PSB/TPGS/Welch's Tropical Carrot solution was briefly mixed and stored for 2 and 6 days at RT. The beverage was centrifuged at 13,000 rpm for 15 min. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. Particle size analysis is presented in the Table 9e.

TABLE 9e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | Welch's Tropical Carrot | 328.7 | 0 |
| 19-Jun-13 | Welch's Tropical Carrot plus Lot# 005.21.4 | 108.7 | 0 |
| 21-Jun-13 | Welch's Tropical Carrot plus Lot# 005.21.4 | 79.0 | 2 |
| 25-Jun-13 | Welch's Tropical Carrot plus Lot# 005.21.4 | 62.4 | 6 |

There was increase of the particle size of formulated PSB upon dilution in Welch's Tropical Carrot beverage form 36.6 to 108.7 nm (Table 9 e). Results suggest contribution of beverage only particles into final particle size of the mixture. The light scattering data are in agreement with HPLC data shows binding of formulated PSB to Welch's Tropical Carrot coarse matrix. Particle size decreased over 6 days from 108.7 to 62.4 nm (Table 9e). Possible emulsification of the beverage matrix components in the presence of formulated PSB that could improve drinking quality of Welch's Tropical Carrot beverage. Data shows chemical stability of formulated PSB in Welch's Tropical Carrot beverage and suggest that "shaking well" will provide 100% of PSB consumption with the beverage.

Example 10. Preparation of PSB/TPGS/Vitamin Water Solution

TABLE 10a

Formulation composition.

| | mg per 21 mL | | |
|---|---|---|---|
| Date | TPGS | PSB | Vitamin Water |
| 14-Jun-13 | 8.5 | 1.7 | 21 mL |

Procedure 1:

PSB/TPGS/Vitamin Water solution preparation: 170 µl of TPGS/PSB emulsion (lot#005.21.4) was added to 21 mL of Vitamin Water beverage. Vitamin Water solution of PSB/TPGS emulsion was briefly mixed and stored for 3 days at RT. 3 Days later 0.6 mL aliquot of PSB/TPGS/Vitamin Water solution was diluted 1:1 with IPA, and HPLC analysis of PSB content was performed (Table 10b).

TABLE 10b

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.086 | ND | N/A | 0 |
| | 17-Jun-13 | 0.086 | 0.082 | 95.83 | 3 |

HPLC Analysis.

"Pterostilbene 310 nm.M" method was used for determination of PSB content. Table 10b shows that after 3 days of storage at RT PSB content in the resultant solution determined by HPLC was similar to calculated amount of PSB added to the beverage. Data suggest that TPGS formulated PSB is stable in Vitamin Water beverage.

Procedure 2:

PSB/TPGS/Vitamin Water solution preparation: 170 μl of PSB/TPGS emulsion (lot#005.21.4) was added to 21 mL of Vitamin Water beverage. PSB/TPGS/Vitamin Water solution was briefly mixed and stored for 3 or 11 days at RT. 3 or 11 Days later, 0.6 mL aliquot of PSB/TPGS/Vitamin Water solution was diluted 1:1 with IPA, filtered through 0.22 μm filter, and HPLC analysis of PSB content was performed (Table 10c).

TABLE 10c

PSB content of resultant solution.

| Preparation Date | HPLC Date | Calculated PSB, mg/mL | HPLC, mg/mL | Recovery, % | Days past preparation |
|---|---|---|---|---|---|
| 14-Jun-13 | | 0.086 | ND | N/A | 0 |
| | 17-Jun-13 | 0.086 | 0.082 | 95.83 | 3 |
| | 25-Jun-13 | 0.086 | 0.087 | 101.68 | 11 |

HPLC Analysis.

"Pterostilbene 310 nm.M" method was used for determination of PSB content. Table 10c shows that after 11 days of storage at RT PSB content in the resultant solution determined by HPLC was similar to calculated amount of PSB added to the beverage. Data suggest that TPGS formulated PSB is stable in Vitamin Water beverage.

Procedure 3:

PSB/TPGS/Vitamin Water solution preparation: 170 μl of PSB/TPGS emulsion (lot#005.21.4) was added to 21 mL of Vitamin Water beverage. PSB/TPGS/Vitamin Water solution was briefly mixed and stored for 3 days at RT. 3 Days later 0.6 mL aliquot of PSB/TPGS/Vitamin Water solution was filtered through 0.22 μm filter, diluted 1:1 with IPA, and HPLC analysis of PSB content was performed (Table 10d).

TABLE 10d

PSB content of resultant solution. Stability.

| Preparation Date | HPLC Date | Calculated PSB, mg/mL | HPLC, mg/mL | Recovery, % | Days past preparation |
|---|---|---|---|---|---|
| 14-Jun-13 | | 0.086 | ND | N/A | 0 |
| | 17-Jun-13 | 0.086 | 0.070 | 81.81 | 3 |

HPLC Analysis.

"Pterostilbene 310 nm.M" method was used for determination of PSB content. Table 10d (recovery %) shows that PSB content of filtered PSB/TPGS/Vitamin Water solution and then diluted with IPA was significantly lower compared to unfiltered (Procedure 1) and/or diluted with IPA and then filtered (Procedure 2) solutions. PSB recovery in filtered Vitamin Water solution of formulated PSB was similar to that of filtered PSB/TPGS water solution (examples 3 and 5). The data provide no evidence of significant binding of formulated PSB to Vitamin Water matrix.

Particle Size Analysis and Stability.

PSB/TPGS/Vitamin Water solution preparation: 170 μl of PSB/TPGS emulsion (lot#005.21.4) was added to 21 mL of Vitamin Water beverage. PSB/TPGS/Vitamin Water solution was briefly mixed and stored for 2 and 6 days at RT. To avoid contribution of coarse beverage matrix to particle size measurement, the beverage was centrifuged at 13,000 rpm for 15 min in an eppendorf centrifuge. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. Particle size analysis is presented in the Table 10e.

TABLE 10e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | Vitamin Water | BDL | 0 |
| 19-Jun-13 | Vitamin Water plus Lot# 005.21.4 | 41.4 | 0 |
| 21-Jun-13 | Vitamin Water plus Lot# 005.21.4 | 39.4 | 2 |
| 25-Jun-13 | Vitamin Water plus Lot# 005.21.4 | 41 | 6 |

Although, there was ~5 nm initial increase of the particle size of the TPGS/PSB emulsion upon dilution in Vitamin Water beverage, the particle size did not change over 6 days. Data suggest that the contribution of beverage only particles into final particle size of the mixture was not significant. Absence of further particle size change suggests stability of formulated PSB in Vitamin Water beverage. Data obtained indicate chemical and particle stability of formulated PSB in Vitamin Water beverage and suggest 100% of PSB consumption with the beverage.

Example 11. Preparation of PSB/TPGS/Gatorade Perform 02 Solution

TABLE 11a

Formulation composition.

| Date | mg per 21 mL | | Gatorade Perform 02 |
|---|---|---|---|
| | TPGS | PSB | |
| 14-Jun-13 | 8.5 | 1.7 | 21 mL |

Procedure 1:

PSB/TPGS/Gatorade Perform 02 solution preparation: 170 µl of TPGS/PSB emulsion (lot#005.21.4) was added to 21 mL of Gatorade Perform 02 beverage. Gatorade Perform 02 solution of PSB/TPGS emulsion was briefly mixed and stored for 3 days at RT. 3 Days later 0.6 mL aliquot of PSB/TPGS/Gatorade Perform 02 solution was diluted 1:1 with IPA, and HPLC analysis of PSB content was performed (Table 11b).

TABLE 11b

PSB content of resultant solution.

| Preparation Date | HPLC Date | PSB content | | | |
|---|---|---|---|---|---|
| | | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.081 | 94.66 | 3 |

HPLC Analysis.

"Pterostilbene 310 nm.M" method was used for determination of PSB content. Table 4b shows that after 3 days of storage at RT PSB content in resultant solution determined by HPLC was similar to calculated amount of PSB added to the beverage. Data suggest that TPGS formulated PSB is stable in Gatorade Perform 02 beverage.

Procedure 2:

PSB/TPGS/Gatorade Perform 02 solution preparation: 170 µl of PSB/TPGS emulsion (lot#005.21.4) was added to 21 mL of Gatorade Perform 02 beverage. PSB/TPGS/Gatorade Perform 02 solution was briefly mixed and stored for 3 or 11 days at RT. 3 or 11 Days later 0.6 mL aliquot of PSB/TPGS/Gatorade Perform 02 solution was diluted 1:1 with IPA, filtered through 0.22 µm filter; HPLC analysis of PSB content was performed (Table 11c).

TABLE 11c

PSB content of resultant solution.

| Preparation Date | HPLC Date | PSB content | | | |
|---|---|---|---|---|---|
| | | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.085 | 99.34 | 3 |
| | 25-Jun-13 | 0.086 | 0.085 | 99.34 | 11 |

HPLC Analysis.

"Pterostilbene 310 nm.M" method was used for determination of PSB content. Table 11c shows that after 11 days of storage at RT PSB content in resultant solution determined by HPLC was similar to calculated amount of PSB added to the beverage. Data suggest that TPGS formulated PSB is stable in Gatorade Perform 02 beverage.

Procedure 3:

PSB/TPGS/Gatorade Perform 02 solution preparation: 170 µl of PSB/TPGS emulsion (lot#005.21.4) was added to 21 mL of Gatorade Perform 02 beverage. PSB/TPGS/Gatorade Perform 02 solution was briefly mixed and stored for 3 days at RT. 3 Days later 0.6 mL aliquot of PSB/TPGS/Gatorade Perform 02 solution was filtered through 0.22 µm filter, diluted 1:1 with IPA, and HPLC analysis of PSB content was performed (Table 11d).

TABLE 11d

PSB content of resultant solution.

| Preparation Date | HPLC Date | PSB content | | | |
|---|---|---|---|---|---|
| | | Calculated PSB, mg/mL | HPLC, mg/mL | Recovery, % | Days past preparation |
| 14-Jun-13 | | 0.086 | ND | N/A | 0 |
| | 17-Jun-13 | 0.086 | 0.071 | 82.98 | 3 |

HPLC Analysis.

"Pterostilbene 310 nm.M" method was used for determination of PSB content. Table 11d (recovery %) shows that PSB content of directly filtered PSB/TPGS/Gatorade Perform 02 solution and then dilution with IPA was significantly lower compared to unfiltered (Procedure 1) and/or diluted with IPA and then filtered (Procedure 2) solutions. PSB recovery in filtered Gatorade Perform 02 solution of formulated PSB was similar to that of filtered PSB/TPGS water solution (examples 3 and 5). No evidence of significant binding of formulated PSB to Gatorade Perform 02 matrix.

Particle Size Analysis and Stability.

PSB/TPGS/Gatorade Perform 02 solution preparation: 170 µl of PSB/TPGS emulsion (lot#005.21.4) was added to 21 mL of Gatorade Perform 02 beverage. PSB/TPGS/Gatorade Perform 02 solution was briefly mixed and stored for 2 and 6 days at RT. To avoid contribution of coarse beverage matrix to particle size measurement, the beverage was centrifuged at 13,000 rpm for 15 min in an eppendorf centrifuge. To measure particle size of the beverage alone, 0.3 mL of supernatant were added to cuvette containing 2.2 mL of distilled water. To determine effect of the beverage on particle size of TPGS/PSP emulsion, 0.6 mL of emulsion (lot #005.21.4) was mixed with 0.6 mL of supernatant, and 0.6 mL of 1:1 mixture was added to the cuvette containing 1.9 mL of distilled water. Particle size analysis is presented in the Table 11e.

TABLE 11e

Particle size and stability.

| Preparation Date | Material | Particle size by intensity, nm | Days past preparation |
|---|---|---|---|
| 19-Jun-13 | Distilled Water plus Lot# 005.21.4 | 36.6 | 0 |
| 19-Jun-13 | Gatorade Perform 02 | 512.8 | 0 |
| 19-Jun-13 | Gatorade Perform 02 plus Lot# 005.21.4 | 41 | 0 |
| 21-Jun-13 | Gatorade Perform 02 plus Lot# 005.21.4 | 39.4 | 2 |
| 25-Jun-13 | Gatorade Perform 02 plus Lot# 005.21.4 | 40.9 | 6 |

There was 4.4 nm initial increase of the particle size of the TPGS/PSB emulsion upon dilution in Gatorade Perform 02 beverage. The particle size did not change over next six days of monitoring. Data suggest that the contribution of beverage only particles to final particle size of the mixture was not significant. Absence of further particle size change suggests stability of formulated PSB in Gatorade Perform 02 beverage. Data indicates chemical and particle stability of formulated PSB in Gatorade Perform 02 beverage and suggest 100% of PSB consumption with the beverage.

Example 12. Preparation of PSB/TPGS Aqueous Emulsion

Determine the Lowest TPGS/PSB ratio producing stable emulsion containing 10 mg/mL of PSB in aqueous media.

TABLE 12a

Formulation composition.

| | | | Weighed, mg (per 100 ml) | | TPGS/PSB |
|---|---|---|---|---|---|
| Date | Lot# | Material | TPGS | PSB | Ratio |
| 01-Jul-13 | 005.30.3 | Mixture | 3117 | 1022 | 3.05 |
| 01-Jul-13 | 005.30.4 | Mixture | 4040 | 1044 | 3.87 |

Table 12a: Amounts of TPGS and PSB were weighed and placed in 400 mL beaker. 9 mL of 95% ethanol were added to the solids, and the beaker containing ethanol mixture of TPGS/PSB was incubated at 60° C. for 20 min until clear. and placed into vacuum oven O/N.

PSB/TPGS emulsions lot#005.30.7 and lot#005.30.8 were prepared on 3 Jul. 2013. Emulsion preparation: The beaker was removed from vacuum oven and 100 mL of distilled water preheated to 60° C. was added to the highly viscous clear film of TPGS/PBS mixture, the beaker was placed in a 60° C. water bath and total mixture was incubated for 30 min to facilitate dissolution. The water TPGS/PBS mixture was mixed on magnetic stirring plate for 2 hrs at RT. Upon clearing of the mixture, the emulsion was filtered through 0.22 μm filter, and particle size and PSB content of the resultant emulsions were determined (Table 12b).

TABLE 12b

Particle size, PSB content, and particle stability of resultant emulsions.

| | | Particle size | PSB | | Formulation Stability | |
|---|---|---|---|---|---|---|
| Manufacturing Date | Lot# | by intensity, nm | Content, mg/mL | Recovery, % | Days past mfg | Particle size nm |
| 3 Jul. 2013 | 005.30.7 | 180.4 | 8.7 | 85.3 | 19 | 216.4 |
| 3 Jul. 2013 | 005.30.8 | 58.0 | 10.10 | 96.7 | 19 | 60.6 |

HPLC Analysis.

"Pterostilbene 310 nm.M" method was used for determination of PSB content. Table 12b shows that 4/1 (TPGS/PSB) ratio was the lowest ratio that allowed formulation of 10 mg/mL of PSB into aqueous media.

Particle Size Analysis and Stability.

The resultant emulsion lot #005.30.8 was stable. It can be seen in Table 12b that particle size did not significantly change over 19 days of monitoring. In contrast, emulsion lot#005.30.7 was not stable (Table 12b) and formed a precipitate over the time of monitoring.

Example 13. Preparation of PSB/PPG-PEG-PPG, Pluronic Emulsions

To investigate the possibility of using alternative emulsifying agents, PPG-PEG-PPG, Pluronic block polymers with 2-7, 7-12, and 12-18 HLB (Hydrophilic-lipophilic balance) range to generate PSB containing stable emulsions containing ~10 mg/mL of PSB. Formulation composition is presented in the Table 13a.

TABLE 13a

Formulation composition.

| Date | Lot# | Block polymers | HLB Range | Material | Weighed, mg (per 100 mL) Block polymer | PSB | Block polymer/PSB Ratio |
|---|---|---|---|---|---|---|---|
| 11 Jul. 2013 | 005.32.1.27 | PPG-PEG-PPG, Pluronic 31Rl | 2-7 | Mixture | 2003 | 1058 | 1.89 |
| 11 Jul. 2013 | 005.32.2.27 | PPG-PEG-PPG, Pluronic 31Rl | 2-7 | Mixture | 4013 | 1014 | 3.96 |
| 11 Jul. 2013 | 005.32.3.712 | PPG-PEG-PPG, Pluronic 17R4 | 7-12 | Mixture | 2036 | 1017 | 2.0 |
| 11 Jul. 2013 | 005.32.4.712 | PPG-PEG-PPG, Pluronic 17R4 | 7-12 | Mixture | 3996 | 1037 | 3.85 |
| 11 Jul. 2013 | 005.32.5.1218 | PPG-PEG-PPG, Pluronic L-64 | 12-18 | Mixture | 1994 | 1014 | 1.97 |
| 11 Jul. 2013 | 005.32.6.1218 | PPG-PEG-PPG, Pluronic L-64 | 12-18 | Mixture | 4007 | 1013 | 3.96 |

Table 13a shows amounts of block polymers and PSB were weighed and placed in 400 mL beaker. 9 mL of 95% ethanol were added to the solids, and the beaker containing ethanol mixture of TPGS/PSB was placed in the water bath and incubated at 60° C. for 20 min until clear. The beaker with ethanol TPGS/PSB solution was placed into vacuum oven O/N.

Emulsion preparation: The beaker was removed from vacuum oven and 100 mL of distilled water preheated to 60° C. was added to the highly viscous clear film of Block polymer/PBS mixture; the beaker was placed in a 60° C. water bath and total mixture was incubated for 30 min to facilitate dissolution. The water Block polymer/PBS mixture was mixed on magnetic stirring plate for 2 hrs at RT. Two hours later the emulsion was filtered through 0.22 μm filter, and particle size and PSB content of the resultant emulsions were determined (Table 13b).

TABLE 13b

Particle size, PSB content, and particle stability of resultant emulsions.

| Manufacturing Date | Lot# | Particle size by intensity, nm | PSB Content, mg/mL | PSB Recovery, % | Formulation Stability Days past mfg | Formulation Stability Particle size nm |
|---|---|---|---|---|---|---|
| 12 Jul. 2013 | 005.32.1.27 | Not Detectable | BDL | NA | NA | NA |
| 12 Jul. 2013 | 005.32.2.27 | Not Detectable | BDL | NA | NA | NA |
| 12 Jul. 2013 | 005.32.3.712 | Not Detectable | BDL | NA | NA | NA |
| 12 Jul. 2013 | 005.32.4.712 | Not Detectable | BDL | NA | NA | NA |
| 12 Jul. 2013 | 005.32.5.1218 | Not Detectable | BDL | NA | NA | NA |
| 12 Jul. 2013 | 005.32.6.1218 | 6907.9 | 0.23 | 2.3 | NA | NA |

HPLC Analysis.

"Pterostilbene 310 nm.M" method was used for determination of PSB content. Table 13b shows that PSB was only detected in Lot#005.32.6.1218 where PPG-PEG-PPG, Pluronic L-64 (HLB Range 12-18) was used for formulation of PSB. However, the measured PSB content (0.23 mg/mL) was far from the target concentration of 10 mg/mL.

Particle Size Analysis and Stability.

Table 13b shows that particle size could be measured only in lot#005.32.6.1218 where PPG-PEG-PPG, Pluronic L-64 (HLB Range 12-18) was used for formulation of PSB. Emulsion was unstable and formed a precipitate.

Example 14. Preparation of PSB/PPG-PEG-PPG, Pluronic Emulsions

To investigate the possibility of using different PPG-PEG-PPG, Pluronic block polymers with 2-7, 7-12, and 12-18 HLB (Hydrophilic-lipophilic balance) range at higher block polymer/PSB ratio to generate PSB containing stable emulsions containing ~10 mg/mL of PSB.

PSB/PPG-PEG-PPG, Pluronic block polymers ethanol mixtures were prepared on 16 Jul. 2013. Formulation composition is presented in the Table 14a.

TABLE 14a

Formulation composition.

| Date | Lot# | Block polymers | HLB Range | Material | Weighed, mg (per 100 mL) Block polymer | PSB | Block polymer/PSB Ratio |
|---|---|---|---|---|---|---|---|
| 16 Jul. 2013 | 005.33.7.27 | PPG-PEG-PPG, Pluronic 31Rl | 2-7 | Mixture | 10205 | 1005 | 10.15 |
| 16 Jul. 2013 | 005.33.8.712 | PPG-PEG-PPG, Pluronic 17R4 | 2-7 | Mixture | 10191 | 1006 | 10.13 |
| 16 Jul. 2013 | 005.33.9.1218 | PPG-PEG-PPG, Pluronic L-64 | 7-12 | Mixture | 10731 | 1003 | 10.70 |

Table 14a shows the amount of block polymers and PSB were weighed and placed in 400 mL beaker. 9 mL of 95% ethanol were added, and the beaker containing ethanol mixture of TPGS/PSB was placed in the water bath and incubated at 60° C. for 20 min until clear. The beaker with ethanol TPGS/PSB solution was placed into vacuum oven O/N.

Emulsion preparation: The beaker was removed from vacuum oven and 100 mL of distilled water preheated to 60° C. was added to highly viscous clear film of Block polymer/PBS mixture, beaker was placed to 60° C. water bath and total mixture was incubated for 30 min to facilitate the dissolution. Water Block polymer/PBS mixture was mixed on magnetic stirring plate for 2 hrs at RT. Two hours later the emulsion was filtered through 0.22 μm filter, and particle size and PSB content of the resultant emulsions were determined (Table 14b).

TABLE 14b

Particle size, PSB content, and particle stability of resultant emulsions.

| | | ART-207 | | |
|---|---|---|---|---|
| Manufacturing Date | Lot# | Particle size by intensity, nm | Content, mg/mL | Recovery, % |
| 17-Jul-13 | 005.33.7.27 | 20576 | BDL | NA |
| 17-Jul-13 | 005.33.8.712 | 420 | 0.13 | 1.3 |
| 17-Jul-13 | 005.33.9.1218 | 113 | 9.47 | 94.4 |

HPLC Analysis.

"Pterostilbene 310 nm.M" method was used for determination of PSB content. Table 14b shows that PSB was detected in Lot#005.33.8.712 (0.13 mg/mL) where PPG-PEG-PPG, Pluronic 17R4 (HLB Range 7-12) and Lot#005.33.9.1218 (9.47 mg/mL) where PPG-PEG-PPG, Pluronic L-64 (HLB Range 12-18) were used for formulation of PSB.

Particle Size Analysis and Stability.

Table 14b shows that particle size decreased from 20576 to 113 nm with increasing of HLB range. However, emulsion Lot#005.33.9.1218 was stable only at 40-50° C. and formed a precipitate at RT. Data obtained demonstrate uniqueness of TPGS (HLB=14.3) as an efficient formulating agent for generating stable emulsions containing 10 mg/mL of PSB in aqueous solutions. Block polymers, including PPG-PEG-PPG, Pluronic L-64 with similar HLB properties to TPGS, were used in an attempt to formulate PSB. None of these formulating agents were able to produce stable 10 mg/mL PSB emulsion at similar or even higher than TPGS/PSB ratios.

Experiment 15. Preparation of PSB/Caffeine/TPGS Emulsion

To prepare emulsion containing 10 mg/ml of PSB/Caffeine (56.2% w/w PSB and 45.0% w/w Caffeine)

TABLE 15a

Formulation composition.

| | | | Weighed, mg (per 100 ml) | | Calculated Weight, mg based on C of A | |
|---|---|---|---|---|---|---|
| Date | Lot# | Material | TPGS | PSB/caffeine | PSB | Caffeine |
| 30 Jul. 2013 | 005.35.1 | Mixture | 5073 | 1022 | 574 | 460 |

5.073 g of TPGS and 1.022 g of PSB/caffeine were weighed and placed in 400 ml beaker. 10 ml of 95% ethanol were added to the solids, and the beaker containing ethanol mixture of TPGS/PSB/caffeine was placed in the water bath, and incubated at 60° C. for 20 min until clear. Then beaker with ethanol TPGS/PSB solution was placed into vacuum oven O/N.

Emulsion preparation: The beaker was removed from vacuum oven and 100 ml of distilled water was added to highly viscous cloudy film of TPGS/PSB/Caffeine mixture, the beaker was placed into a 60° C. water bath and the total mixture was incubated for 30 min to facilitate dissolution. The water TPGS/PSB/Caffeine mixture was mixed on magnetic stirring plate for 2 hrs at RT. Upon clearing of the mixture, particle size and PSB and caffeine content of the resultant emulsion was determined (Table 15b).

TABLE 15b

Particle size, PSB content, and Caffeine content of resultant emulsion.

| | | Particle size | PSB | | Caffeine | |
|---|---|---|---|---|---|---|
| Manufacturing Date | Lot# | by intensity, nm | Content, mg/ml | Recovery, % | Content, mg/ml | Recovery, % |
| 31 Jul. 2013 | 005.35.3 | 13.1 | 5.66 | 99 | 4.53 | 98 |

HPLC Analysis.

"Pterostilbene 280.M." method was used for determination of PSB and caffeine content. PSB content and Caffeine content in resultant emulsion determined by HPLC ("Pterostilbene 280 NM" method) was PSB was 5.66 mg/mL and caffeine 4.53 mg/mL. Recovery is based on the weighed amount of the pterostilbene/caffeine co-crystal and the weight % provided by the Chromadex C of A. Data indicate that 99% of the PSB used for preparation of this formulation was incorporated into TPGS particles (Table 15b).

TABLE 15c

Particle size, PSB content, and stability of resultant emulsion.

| Manufacturing Date | Lot# | Days past mfg | Particle size by intensity, nm | PSB Content, mg/ml | PSB Recovery, % | Caffeine Content, mg/ml | Caffeine Recovery, % |
|---|---|---|---|---|---|---|---|
| 31 Jul. 2013 | 005.35.3 | 6 | 13.1 | 5.85 | 102 | 4.68 | 102 |

Particle Size Analysis and Stability.

The ratio of TPGS to PSB in this emulsion is 8.8:1 and this large ratio produces the small particle size of 13.1 nm. The resultant emulsion was stable. Tables 15b and 15c show that particle size did not change over 6 days of monitoring. After 30 days the emulsion is visually unchanged.

Experiment 16. Preparation of PSB/Caffeine/TPGS Emulsion

To prepare emulsion containing 10 mg/ml of PSB from the PSB/Caffeine co-crystal (56.2% w/w PSB and 45.0% w/w Caffeine).

TABLE 16a

Formulation composition.

| Date | Lot# | Material | Weighed, mg (per 100 ml) TPGS | Weighed, mg (per 100 ml) PSB/caffeine | Calculated Weight, mg based on C of A PSB | Calculated Weight, mg based on C of A Caffeine |
|---|---|---|---|---|---|---|
| 1 Aug. 2013 | 005.36.2 | Mixture | 5018 | 1779 | 1000 | 801 |

5.018 g of TPGS and 1.779 g of PSB/caffeine were weighed and placed in 400 ml beaker. 10 ml of 95% ethanol were added to the solids, and the beaker containing ethanol mixture of TPGS/PSB/caffeine was placed in the water bath, and incubated at 60° C. for 20 min until clear. Beaker with ethanol TPGS/PSB solution was placed into vacuum oven O/N.

Emulsion preparation: The beaker was removed from oven and 100 ml of distilled water was added to highly viscous cloudy film of TPGS/PSB/Caffeine mixture, beaker was placed to 60° C. water bath and total mixture was incubated for 30 min to facilitate the dissolution. Then water TPGS/PSB/Caffeine mixture was mixed on magnetic stirring plate for 2 hrs at RT. Upon clearing of the mixture, particle size, PSB and caffeine content of the resultant emulsion was determined (Table 16b). The emulsion is transparent but hazy. The emulsion was filtered through 0.22 μm filter and particle size, PSB and caffeine content were measured again. The haziness did not change after filtration.

TABLE 16b

Particle size, PSB content, and Caffeine content of resultant emulsion.

| Manufacturing Date | Lot# | Particle size by intensity, nm | PSB Content, mg/ml | PSB Recovery, % | Caffeine Content, mg/ml | Caffeine Recovery, % |
|---|---|---|---|---|---|---|
| 2 Aug. 2013 | 005.36.3 | 33.4 | 9.65 | 97 | 7.67 | 96 |
| 2 Aug. 2013 | 005.36.3 filtered | 33.5 | 9.75 | 98 | 7.73 | 97 |

HPLC Analysis.

"Pterostilbene 280.M." method was used for determination of PSB and caffeine content. PSB content and Caffeine content in resultant emulsion determined by HPLC ("Pterostilbene 280 NM" method) was PSB was 9.65 mg/mL and caffeine 7.67 mg/mL. Particle size, PSB and caffeine content are not significantly different in the unfiltered emulsion as compared to the filtered emulsion. Recovery is based on the weighed amount of the PSB/caffeine co-crystal and the weight % provided by the Chromadex C of A. Data show 97% of the PSB used for preparation was incorporated into TPGS particles (Table 16b).

Particle Size Analysis.

The ratio of TPGS to PSB in this emulsion is 5:1 and this ratio resulted in a particle size of 33.4 nm which is larger than the particle size in Experiment 15 and shows that a lower ratio of PSB and TPGS results in larger particle sizes. The presence of caffeine does not appear to influence the emulsification of PSB. Three days after manufacture, the filtered emulsion was found to have crystallized. The analytical data of the supernatant is shown in Table 16c below. Both PSB and Caffeine have precipitated from solution. The ratio of TPGS to PSB in the supernatant or mother liquors is 9.1:1. The results for particle size and PSB and caffeine content of the supernatant suggest the maximum stable concentrations of PSB and caffeine and minimum ratio of PSB to TPGS in an emulsion for a given concentration of TPGS (50 mg/mL). The ratio of TPGS to PSB in the supernatant is 9.1:1.

TABLE 16c

Particle size, PSB content, and stability of resultant emulsion.

| Manufacturing Date | Lot# | Days past mfg | Particle size by intensity, nm | PSB Content, mg/ml | PSB Recovery, % | Caffeine Content, mg/ml | Caffeine Recovery, % |
|---|---|---|---|---|---|---|---|
| 2 Aug. 2013 | 005.36.3 filtered | 3* | 13.8 | 5.49 | 55 | 4.58 | 57 |

*the emulsion crystallized, analysis is of the supernatant.

Dilutions.

On 9 Aug. 2013 (one week after preparation) Lot#005.36.3 was warmed to 65° C. for 1.5 hours. The crystals had dissolved and the solution was cloudy. Upon cooling and setting for 2 hours on the bench, the solution cleared and two phases were observed. Vigorous hand agitation for 15 seconds resulted in a solution which appeared to be homogenous. The particle size analysis result of the solution with the crystals re-dissolved was 31.5 nm. Dilutions of the preparation were made to evaluate the effect of concentration of the PSB and caffeine on emulsion stability. Dilutions: none, 1:1, 1:10, 1:20 and 1:100 were prepared in 50 mL centrifuge tubes and allowed to set for three days. On day three the no dilution sample had crystallized and the 1:1 dilution sample had a few crystals. The other dilutions had no crystals. Results suggest that when the PSB concentration is below 0.6 mg/mL and the caffeine concentration similarly low (below 0.5 mg/mL), a stable emulsion can be readily generated.

Experiment 17

Preparation of PSB/Caffeine/TPGS Emulsion

To prepare emulsion containing 11.2 mg/ml of PSB from the PSB/Caffeine co-crystal (56.2% w/w PSB and 45.0% w/w Caffeine).

TABLE 17a

Formulation composition.

| Date | Lot# | Material | Weighed, mg (per 100 ml) TPGS | Weighed, mg (per 100 ml) PSB/caffeine | Calculated Weight, mg based on C of A PSB | Calculated Weight, mg based on C of A Caffeine |
|---|---|---|---|---|---|---|
| 1 Aug. 2013 | 005.36.1 | Mixture | 5003 | 2.008 | 1128 | 904 |

5.003 g of TPGS and 2.008 g of PSB/caffeine were weighed and placed in 400 ml beaker. 10 ml of 95% ethanol were added to the solids, and the beaker containing ethanol mixture of TPGS/PSB/caffeine was placed in the water bath, and incubated at 60° C. for 20 min until clear. Then beaker with ethanol TPGS/PSB solution was placed into vacuum oven O/N.

Emulsion preparation: The beaker was removed from vacuum oven and 100 ml of distilled water was added to highly viscous cloudy film of TPGS/PSB/Caffeine mixture, beaker was placed to 60° C. water bath and total mixture was incubated for 30 min to facilitate dissolution. Water TPGS/PSB/Caffeine mixture was mixed on magnetic stirring plate for 2 hrs at RT. Upon clearing of the mixture, particle size, PSB and caffeine content of the resultant emulsion was determined (Table 17b). The emulsion is transparent but hazy.

TABLE 17b

Particle size, PSB content, and Caffeine content of resultant emulsion.

| Manufacturing Date | Lot# | Particle size by intensity, nm | PSB Content, mg/ml | PSB Recovery, % | Caffeine Content, mg/ml | Caffeine Recovery, % |
|---|---|---|---|---|---|---|
| 2 Aug. 2013 | 005.36.4 | 42.8 | 10.79 | 95 | 8.56 | 96 |

HPLC Analysis.

"Pterostilbene 280.M." method was used for determination of PSB and caffeine content. PSB content and Caffeine content in resultant emulsion determined by HPLC ("Pterostilbene 280 NM" method) was PSB was 10.79 mg/mL and caffeine 8.56 mg/mL. Recovery is based on the weighed amount of the pterostilbene/caffeine co-crystal and the weight % provided by the Chromadex C of A. Data indicate that 95% of the PSB used for preparation of this formulation was incorporated into TPGS particles (Table 17b).

Particle Size Analysis.

The ratio of TPGS to PSB in this emulsion is 4.4:1 and this ratio results in a particle size of 42.8 nm which is larger than the particle size in Experiment 16 and again shows that a lower ratio of PSB and TPGS result in larger particle sizes. The presence of caffeine does not appear to influence the emulsification of PSB. Three days after manufacture, the filtered emulsion was found to have crystallized. Data of the supernatant or mother liquors is shown in Table 17 c below. Both PSB and caffeine have come out of solution. The ratio of TPGS to PSB in the supernatant or mother liquors is 9.1:1. The results for particle size and PSB and caffeine content of the supernatant or mother liquors suggests the maximum stable concentrations of PSB and caffeine and minimum ratio of PSB to TPGS in an emulsion for a given concentration of TPGS (50 mg/mL). The ratio of TPGS to PSB in the supernatant is again 9.1:1. The emulsion of experiment 17 gives similar results to that of experiment 16; a critical ratio of 9 to 1 of TPGS to PSB in the presence of caffeine is necessary to form a stable emulsion of PSB at greater than 0.6 mg/mL PSB.

TABLE 17 c

Particle size, PSB content, and particle stability of resultant emulsion.

| Manufacturing Date | Lot# | Days past mfg | Particle size by intensity, Nm | PSB Content, mg/ml | PSB Recovery, % | Caffeine Content, mg/ml | Caffeine Recovery, % |
|---|---|---|---|---|---|---|---|
| 2 Aug. 13 | 005.36.4 | 3* | 13.5 | 5.51 | 49 | 4.63 | 51 |

*the emulsion crystallized, analysis is of the supernatant

Experiment 18

Preparation of a Cremophor® ELP Emulsion

To prepare emulsion containing 5% v/v of Cremophor in distilled water and measure particle size.

TABLE 18a

Formulation composition.

| Date | Lot# | Material | Volume, mL Cremophor | Volume, mL Water |
|---|---|---|---|---|
| 27-Aug-13 | 005.39.1 | Mixture | 1 mL | 19 mL |

Distilled water, 19 mL, was added to 1 mL of Cremophor in a 20 mL vial, capped and heated to 60° C. then mixed to form a nearly clear solution.

TABLE 18b

Particle size of resultant emulsion.

| Manufacturing Date | Lot# | Particle size by intensity, nm |
|---|---|---|
| 27-Aug-13 | 005.39.1 | 12.6 |
| 28-Aug-13 | 005.39.1 | 12.8 |

Experiment 19

Preparation of PSB/Cremophor ELP Emulsion

To prepare emulsion containing 1.0 mg/ml of PSB and 5 mg/mL Cremophor.

TABLE 19a

Formulation composition.

| Date | Lot# | Material | Weighed, mg (per 100 ml) Cremophor | Weighed, mg (per 100 ml) PSB |
|---|---|---|---|---|
| 25-Aug-13 | 005.38.1 | Mixture | 5038 | 1007 |

5.038 g of Cremophor and 1.007 g of PSB were weighed and placed in 200 ml beaker. Cremophor is a viscous oil at RT. The beaker was placed in a 65° C. water bath and over 30 minutes the Cremophor dissolved the PSB based on visual observation. 10 ml of 95% ethanol were added to the oily mixture, and the beaker containing the ethanol mixture of Cremophor/PSB was placed in the water bath, and incubated at 60° C. for 20 min until the oil dissolved, and ethanol was evaporated with a Nitrogen stream. The residual ethanol Cremophor/PSB mixture was placed into vacuum oven overnight.

Emulsion preparation: The beaker was removed from vacuum oven and 100 ml of distilled water was added to the highly viscous clear film of Cremophor/PSB mixture, the beaker was placed to 60° C. water bath and the total mixture was incubated for 30 min to facilitate dissolution. The water Cremophor/PSB mixture was mixed on magnetic stirring plate for 1 hr at RT. The mixture never cleared and retained a milky appearance. Particle size of the resultant suspension was determined immediately and the following day (Table 19b). No settling or crystallization at days one and three.

TABLE 19b

Particle size of resultant suspension.

| Manufacturing Date | Lot# | Particle size by intensity, nm |
|---|---|---|
| 27-Aug-13 | 005.38.1 | 286.9 |
| 28-Aug-13 | 005.38.1 | 339.3 |

Particle Size Analysis.

The ratio of Cremophor to PSB in this emulsion is 5:1. This ratio resulted in a particle size of approximately 300 nm.

Experiment 20

Preparation of PSB/Caffeine/Cremophor Emulsion

To prepare emulsion containing 10 mg/ml of PSB from the PSB/Caffeine co-crystal (56.2% w/w PSB and 45.0% w/w Caffeine) with Cremophor.

TABLE 20a

Formulation composition.

| Date | Lot# | Material | Weighed, mg (per 100 ml) Cremophor | Weighed, mg (per 100 ml) PSB/caffeine | Calculated Weight, mg based on C of A PSB | Calculated Weight, mg based on C of A Caffeine |
|---|---|---|---|---|---|---|
| 25-Aug-13 | 005.38.2 | Mixture | 5000* | 1773 | 996 | 798 |

*Actual weight not recorded (5 mL)

Cremophor (5 mL) and 1.773 g of PSB/caffeine were weighed and placed in 200 ml beaker. 10 ml of 95% ethanol were added to the solids, and the beaker containing ethanol mixture of Cremophor/PSB/caffeine was placed in the water bath, and incubated at 60° C. for 30 min. The solution did not clear and upon cooling appeared to crystallize. 10 mL of 95% ethanol was added and incubated at 60° C. for an additional 30 min until the solution cleared. During evaporation with a nitrogen stream the solution crystallized. The beaker with ethanol/Cremophor/PSB/caffeine solids was placed into vacuum oven O/N.

Emulsion preparation: The beaker was removed from vacuum oven and 100 ml of distilled water was added to solids of Cremophor/PSB/Caffeine, the beaker was placed to 60° C. water bath and total mixture was incubated for 30 min to facilitate dissolution. The water/Cremophor/PSB/Caffeine mixture was mixed on magnetic stirring plate for 1 hr at RT. The mixture retained a milky appearance. Particle size of the resultant suspension was determined in Table 20b. No settling or crystallization noted on days one and three.

TABLE 20b

Particle size of resultant suspension.

| Manufacturing Date | Lot# | Particle size by intensity, nm |
| --- | --- | --- |
| 27-Aug-13 | 005.38.2 | 375.6 |
| 28-Aug-13 | 005.38.2 | 371.2 |

Particle Size Analysis.

The ratio of Cremophor to PSB in this emulsion is approximately 5:1. This ratio resulted in a particle size of approximately 375 nm and has large particle size.

The present application discloses unique compositions with specific ratios of formulation components that produce stable RVT- or PSB-containing nanoparticles in the range from 20 to 40 nm. The nanoparticulate emulsion is stable in a variety of beverages providing the calculated beneficial dose of resveratrol or pterostilbene, or a mixture thereof, per serving. The above compositions are prepared with a RVT- and PSB-containing nanoparticles where the stable, soluble compositions of RVT- and PSB-containing nanoparticles resulted in similar stable and clear solutions where a mixture of RVT- and PST-containing nanoparticles were prepared.

The foregoing examples of the related art and limitations are intended to be illustrative and not exclusive. While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

What is claimed:

1. A stable and homogeneous aqueous formulation comprising:
   a) a composition selected from the group consisting of a pterostilbene-caffeine co-crystal complex, and a resveratrol-caffeine co-crystal complex; and
   b) an emulsifying agent in an amount sufficient to solubilize the pterostilbene-caffeine co-crystal complex, a resveratrol-caffeine co-crystal complex, to form the stable and homogeneous formulation,
   wherein the emulsifying agent is TPGS, the ratio of emulsifying agent to resveratrol or pterostilbene is in the range of 3:1 to 10:1, the resultant emulsion comprises a particle size of between 25 and 100 nanometers, the pterostilbene-caffeine co-crystal complex, a resveratrol-caffeine co-crystal complex in water is at a co-crystal complex:water (wt:wt) ratio of 10:90, 20:80, 30:70, 40:60, 50:50, 60:40, 70:30, 80:20, 90:10, 95:5 or more,
   and the formulation is an emulsion or a clear solution, and the formulation is stable for a period of at least 6 months or 12 months at RT, or at least 12 months at about 12-15° C.

2. The stable and homogeneous aqueous formulation of claim 1, wherein the solution is in water.

3. The stable and homogeneous aqueous formulation of claim 1, wherein the formulation comprising the pterostilbene-caffeine co-crystal complex, a resveratrol-caffeine co-crystal complex in water is at a co-crystal complex:water (wt:wt) ratio of 10:90, 20:80, 30:70, 40:60, 50:50, 60:40, 70:30, 80:20 or 90:10.

* * * * *